US009222100B2

(12) United States Patent
Allen et al.

(10) Patent No.: US 9,222,100 B2
(45) Date of Patent: Dec. 29, 2015

(54) METHODS AND DNA CONSTRUCTS FOR AUTOREGULATING TRANSGENE SILENCING

(75) Inventors: Edwards Allen, O'Fallon, MO (US); Larry A. Gilbertson, Chesterfield, MO (US); Sergey I. Ivashuta, Ballwin, MO (US); James K. Roberts, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/862,078

(22) Filed: Aug. 24, 2010

(65) Prior Publication Data

US 2012/0054919 A1 Mar. 1, 2012

(51) Int. Cl.
*C12N 15/82* (2006.01)
(52) U.S. Cl.
CPC ........ *C12N 15/8218* (2013.01); *C12N 15/8216* (2013.01)
(58) Field of Classification Search
USPC ................................................. 800/285, 286
See application file for complete search history.

(56) References Cited

U.S. PATENT DOCUMENTS

| | | | |
|---|---|---|---|
| 4,769,061 A * | 9/1988 | Comai | 504/206 |
| 4,810,648 A | 3/1989 | Stalker | |
| 5,463,175 A | 10/1995 | Barry et al. | |
| 5,500,365 A | 3/1996 | Fischhoff et al. | |
| 5,597,717 A | 1/1997 | Guerineau et al. | |
| 5,627,061 A | 5/1997 | Barry et al. | |
| 5,646,024 A | 7/1997 | Leemans et al. | |
| 5,689,052 A * | 11/1997 | Brown et al. | 800/302 |
| 5,767,366 A | 6/1998 | Sathasivan et al. | |
| 6,414,222 B1 | 7/2002 | Gengenbach et al. | |
| 2001/0023067 A1 | 9/2001 | Wassenegger et al. | |
| 2003/0083480 A1 | 5/2003 | Castle et al. | |
| 2003/0115626 A1 | 6/2003 | Weeks et al. | |
| 2004/0200874 A1 | 10/2004 | Menna | |
| 2006/0123510 A1 | 6/2006 | Odell et al. | |
| 2006/0174380 A1 | 8/2006 | Carrington et al. | |
| 2007/0192903 A1 | 8/2007 | Heck et al. | |
| 2008/0066206 A1 | 3/2008 | Allen et al. | |
| 2008/0201801 A1 | 8/2008 | Allen et al. | |
| 2009/0117539 A1 | 5/2009 | Gilbertson et al. | |

FOREIGN PATENT DOCUMENTS

| | | | |
|---|---|---|---|
| WO | WO 99/27116 A2 | 6/1999 | |
| WO | WO 02063039 A2 * | 8/2002 | |
| WO | WO 2010/002984 A1 | 1/2010 | |

OTHER PUBLICATIONS

Broderson et al. The diversity of RNA silencing pathways in plants (2006) Trends in Gen. 22: 268-280.*
Herr et al. RNA polymerase IV directs silencing of endogenous DNA (2005) Science 308: 118-120.*
Vazquez et al. The biosythetic pathways and biological scopes of plant small RNAs (2010) Trends in Plant Sci. 15: 337-345.*
Weising et al. Foreign genes in plants: transfer, structure, expression, and applications (1988) Annu. Rev. Genet. 22: 421-77.*
Hruz et al. Genvestigator V3: a referenece expresion database for the meta-analysis of transcriptomes (2008) Adv. Bioinformatics, Article ID 420747.*
Chompreeda et al. (1984) J. Food Sci. 49: 566-568.*
Xie et al (2004) PLoS Biol. 2: 342-652.*
Alleman et al., "An RNA-dependent RNA polymerase is required for paramutation in maize," *Nature*, 442:295-298 (2006).
Allen et al., "microRNA-Directed Phasing during Trans-Acting siRNA Biogenesis in Plants," *Cell*, 121: 207-221(2005).
Arciga-Reyes et al., "UPF1 is required for nonsense-medicated mRNA decay (NMD) and RNAi in Arabidopsis," *The Plant Journal*, 47:480-489 (2006).
Chan et al., "Gardening the Genome: DNA Methylation in *Arabidopsis thaliana*," *Nature Reviews*, 6:351-360 (2005).
Denli et al, "RNAi: an ever-growing puzzle," *TRENDS in Biochemical Sciences*, 28(4):196-201 (2003).
Elmayan et al., "Arabidopsis Mutants Impaired in Cosuppression," *The Plant Cell*, 10:1747-1757 (1998).
Fahlgren et al., "Regulation of Auxin Response Factors by TAS3 ta-siRNA Affects Developmental Timing and Patterning in *Arabidopsis*," *Current Biology*, 16:939-944 (2006).
Khvorova et al., "Functional siRNAs and miRNAs Exhibit Strand Bias," *Cell*, 115:209-216 (2003).
Kooter et al., "Listening to the silent genes: transgene silencing, gene regulation and pathogen control," *Trends in Plant Science*, 4(9) 340-347 (1999).
Matzke et al., "RNAi-Mediated Pathways in the Nucleus," *Nature Reviews*, 6:24-35 (2005).
Reynolds et al., Rational siRNA design for RNA interference, *Nature Biotechnology*, 22(3):326-330 (2004).
Schwach et al., An RNA-Dependant RNA Polymerase Prevents Meristem Invasion by Potato Virus X and Is Required for the Activity But Not the Production of a Systemic Silencing Signal, *Plant Physiology*, 138:1842-1852 (2005).
Mourrain et al.,"*Arabidopsis* SGS2 and SGS3 Genes Are Required for Posttranscriptional Gene Silencing and Natural Virus Resistance," *Cell*, 101:533-542 (2000).
Xie et al., "Genetic and Functional Diversification of Small RNA Pathways in Plants," *PLoS Biology*, 2(5):0642-0652 (2004).

* cited by examiner

*Primary Examiner* — Steven Bernacki
(74) *Attorney, Agent, or Firm* — Amanda Carmany-Rampey; Arnold & Porter LLP; David R. Marsh

(57) ABSTRACT

This invention provides a method to autoregulate expression of a transgene susceptible to sRNA silencing by concomitantly transcribing RNA from DNA of a transgene and RNA from DNA from at least one sRNA silencing pathway gene. An aspect of the invention provides use of a recombinant DNA construct that includes DNA of a transgene and DNA of an sRNA silencing regulator. Also disclosed are transgenic cells and organisms having in their genome a recombinant DNA construct that includes DNA of a transgene and DNA of an sRNA silencing regulator.

11 Claims, 6 Drawing Sheets

SEQUENCE LISTING

```
<160> NUMBER OF SEQ ID NOS: 7

<210> SEQ ID NO 1
<211> LENGTH: 698
<212> TYPE: DNA
<213> ORGANISM: Zea mays

<400> SEQUENCE: 1
cacacttcgc atttgcatcc atccctcgct cggttatgaa attttttaaa ccccttccga      60
tcctaaataa aacggaaatc aaccccacaa aaccccctgcg taaagagacc caattgctat    120
ctcctccagc atccacccaa cggatccgcg gcaaccgacc acccatggga tcgctccggg    180
gcgcggcagc ctcctccgcg gcgccgcgcg cgggcgacct ggtgaccacg caggttagcc    240
ttggtggatt tgatgccacc gtcaaggcgc tcgatctcgc cgacttcctc gagttgaatg    300
cgggctcggt ctggcgctgc cgcctcaaga cctcctggac tccgccggac gcctatcccg    360
acttccttct ccccaccgtc acctccgccg ccgcgccgcc gccacagtac gatcgcgtgc    420
ctccgcacgc cttcgtccac tttgcgcgcc cggagggcgc gcgcgccgcc actctccgct    480
ctggcgtcgt cactggttcc ttgacccctg tgcgggtcgg tcggtggtgc tagggtcagc    540
agttgtctgg tgtctgtagc ctctctggct atccgttctt tggtgtgaaa tggaattcca    600
atcgtgtggg aatggatctc tgttcgattg ttcaattggc ccatattcca tctttggatc    660
```

```
ttagttttgc actaatggcg caagcctttt cgaaaacc                            698
```

<210> SEQ ID NO 2
<211> LENGTH: 2040
<212> TYPE: DNA
<213> ORGANISM: Zea mays

<400> SEQUENCE: 2

```
cttgcatgcc tgcagctgcc agaaggcgtc gtcgggaacg ccttgggtgg tgagcagcgt     60
tatgatctgg cggttcaaga acgctggctg gaacttggtc caggacacca cttccagcac    120
ggtgtgcgtg gactggaact tcctcatgct gggccgaagc gacatcctcc gcgtcccacg    180
gtcttcttgt cccggccccg gcggccagac agccacgacg cccttgaacc ccgcgtacct    240
gatctggtac gcgacggggc gaacctgtcg ccagcggc agcatctcgg cgacctccag     300
cgcgaggtcc tccgtgatca ccccgatccc gtcggagaag ttgtacccgt tgcgcgtaac    360
gtcctcgagg tcctcgtcca cctcgccggg ctgcatcgtc accgtcgcgt aggaagacgt    420
gaagcacagc cccatccgag cggcgtgctt cgcggggttc ctgatcggga actgccccat    480
ccactccttt atgcctgcca ccgttgtcgc tccgtcctcc gcgaagaacc aggccgactt    540
ttgcttcagc tggctggctg agaacgcgag gaacgagtac ctcctgccac acatgatgag    600
cccctccgtc agggccgtct ggacacgcct gtagacgctt gtcatctgcc gggatgtgct    660
gggcgtcgac gtcgagggca ccgcacgcgag ggtcagcgcg ttagggttca gcggcagcat    720
accctcgtcc gtaaaagtat ccctcaagaa gcgatctgac agctactggt aatgcctgat    780
gactcggatg gagcgctcca cttgaggcgg tatacagtat tccatggctg gagacttgta    840
gcgacgatca gccttcggac ctcagcatcg caatcactag cctttcttct tctgctgctg    900
ctgctgctgc gacagacaag atcgagattc ttggcagccc tgtcctgcgc gttcttcaac    960
ctccagcatg gattatcaca gactccaagc tttgcaccga acagttccgt cagcgcagca   1020
acgttcacat cttcgcgtgt cctcatcagc aaaccgaaga actccggtgt catctggtgc   1080
ggattgacta ccccgttgtg catcagcacg ttgaccaagt atagctccgg gaaccgtagc   1140
cctgcgtcgt cgtcgtgctc gtgccgcggg gagaagaacg cgtcccgcat cggctgcacc   1200
aagcctgcct cctcgagcac ggtgaagccc cgacaccgtc tgtcgcgtac gtggacgggg   1260
accccctgcc tctgcatgca ctccagcgcg accctcatcg tcggccagaa ctgcaccgcg   1320
aaggagaccc tgtacgccaa gcaccggccg atggcgccgc tctgggtcac gtcggtggtc   1380
cgtatccacg ggtcgtcgtc ggcgtcgacg agttggaagg gcacgcggcc gtggacgtcg   1440
tcgcccgacg tgcggtagta cacgagggggc gcggcggaga gccggaggac cagcgagtcg   1500
tcggcctgga acgccagggc ctcggtgacg tgggcgagcg cgaattcgag cttcacgtcg   1560
cagcacagca gcgccgcggg ccggcgcctg tcggggcacg tgaaggcggt gtagcgggcg   1620
aacagcagcc ggcagctgcc gccagacggg tccaccacga agtcgagcgc cgaggcgctg   1680
tcgtcggtcc cgcgccacgc gacgaggaag gtgtccggcg ccacgacgtc gccgatctcg   1740
atgcgcgagt cggggaagag catcggtttg gcggcgtcgg tgacaccatc ccgccggcgc   1800
gccgcatggc catgtaccag gtgtctgctc tgcgcgagga tgcgcgtcgt gaagaagtcg   1860
ccagcgcggt ccgcggcatt gcggtgctcg aagtggacga aggcatgagg ggccacgcga   1920
```

```
ccgtcccgcg gcggctcgtc ctggtcctgg tggaatacgg cggcggcggc ggcggtgtgg   1980
actgagagct ggaagtccgg gtaggactcg ggcggtgtga cggaagtctt gatcctgcag   2040

<210> SEQ ID NO 3
<211> LENGTH: 225
<212> TYPE: DNA
<213> ORGANISM: Nicotiana benthamiana

<400> SEQUENCE: 3
gcatgggcag gatatttgtt ccttcgggag gtggttgatg ggctgtctgg atgaattagg     60
tgagcttgag caaggccaat gctttattca agtgtctatc ccttccttgg agaattgttt    120
tattaagcat ggtctgaaat ttcgggtatc aagaaaaatc ttcaagtagt aaaggacctt    180
gttgtaattg caaagaacct gtgtcttcat ccaggggatg tgagg                    225

<210> SEQ ID NO 4
<211> LENGTH: 230
<212> TYPE: DNA
<213> ORGANISM: Nicotiana benthamiana

<400> SEQUENCE: 4
acatcccctg gatgaagaca cgggttcttt gcaattacaa caaggcccctt tactacttga    60 agatttttct ttatatcaga aaatttcgga ccatgcttaa taaaacaatt ctccaaagaa    120
gggcttgaca cttgaataaa gcattggccc tgctcaagct cacctaattc atccaaacag    180
cccatcaacc accttcccga aggaacaaat tcctgcccag ccgctgcgat                230

<210> SEQ ID NO 5
<211> LENGTH: 166
<212> TYPE: DNA
<213> ORGANISM: Zea mays

<400> SEQUENCE: 5
gcgacctggt gaccacgcag gttagccttg gtggatttga tgccaccgtc aaggcgctcg     60
atctcgccga cttcctcgag ttgaatgcgg gctcggtctg cgctgccgc ctcaagacct    120 cctggactcc gccggacgcc tatcccgact tccttctccc caccgt                   166

<210> SEQ ID NO 6
<211> LENGTH: 184
<212> TYPE: DNA
<213> ORGANISM: Zea mays

<400> SEQUENCE: 6
ggttcaagaa cgctggctgg aacttggtcc aggacaccac ttccagcacg gtgtgcgtgg     60
actcgaactt cctcatgctg ggccgaagcg acatcctccg cgtcccacgg tcttcttgtc    120
ccggccccgg cggccagaca gccacgacgc ccttgaaccc cgcgtacctg atctggtacg    180
cgga                                                                  184

<210> SEQ ID NO 7
<211> LENGTH: 272
<212> TYPE: DNA
<213> ORGANISM: Zea mays

<400> SEQUENCE: 7
tacctgaagc acgattccca gagctacaag cttgaggttc tctttgagga catcaatgag     60
tgctttgggt gccactcga tgggacgggc gccatcttgc tgcagctgac ttatgcacca    120
```

```
agaatacaca ttgcaatttc tgggtctaca gttaaatcaa ggtttacaga tgatcgcttt      180
catgcatgca aggaggacgc caaatttgca tgggtcagag cactagattt cacacctaat      240
agctcttttg gcgagtgttc cactcttgtc ct                                    272
```

METHODS AND DNA CONSTRUCTS FOR AUTOREGULATING TRANSGENE SILENCING

INCORPORATION OF SEQUENCE LISTING

The sequence listing contained in the file named "38-21 (54775).txt", which is 6 kilobytes (measured in MS-Windows) created on 24 Aug. 2010, is filed herewith by electronic submission and incorporated herein by reference.

FIELD OF THE INVENTION

Disclosed herein are recombinant DNA constructs for autoregulating the expression of a transgene susceptible to small RNA (sRNA) silencing and methods of making and using such constructs.

SUMMARY OF THE INVENTION

This invention provides a method to autoregulate expression of a transgene susceptible to sRNA silencing by concomitantly transcribing RNA from DNA of a transgene and RNA from DNA of at least one sRNA silencing pathway gene. A transgene is susceptible to sRNA silencing when transcription of the transgene to RNA initiates sRNA silencing of the transgene. Such silencing is observed in plants with highly expressed transgenes imparting novel traits, e.g., herbicide tolerance and pest tolerance. By concomitantly transcribing RNA from DNA of a transgene and RNA from DNA from an sRNA silencing pathway gene, initiation of sRNA silencing also suppresses expression of the sRNA silencing pathway gene. This concomitant transcription of both the transgene and the sRNA silencing pathway gene provides for autoregulation of expression of the transgene with less susceptibility to sRNA silencing.

An aspect of the invention provides a recombinant DNA construct that includes DNA of a transgene and DNA of an sRNA silencing regulator. The sRNA silencing regulator includes DNA from at least one sRNA silencing pathway gene. The recombinant DNA construct is transcribed in a transgenic host cell so that the transgene and the sRNA silencing regulator are concomitantly transcribed to RNA. In some aspects of the invention the DNA construct comprises a single promoter to initiate transcription of RNA from DNA of the transgene and RNA from DNA of the sRNA silencing regulator.

Another aspect of the invention provides for a recombinant cell having in its genome the recombinant DNA construct that includes DNA of a transgene and DNA of at least one sRNA silencing regulator. The invention further provides a transgenic organism having the recombinant DNA construct and products prepared from the transgenic organism, e.g., where the transgenic organism is a plant.

DETAILED DESCRIPTION OF THE INVENTION

As used herein "concomitant" means occurring or existing concurrently and "concomitantly transcribing" refers to RNAs that are produced from DNA at the same time and exist in the same cell.

This invention discloses a method to autoregulate expression of a transgene susceptible to sRNA silencing by concomitantly transcribing RNA from DNA of a transgene and RNA from DNA of at least one sRNA silencing pathway gene.

Small RNA (sRNA) silencing is described in the art as homology-dependent gene silencing, e.g., sequence-specific inhibition of gene expression, and involves diverse sRNA silencing pathways whereby silencing may occur at transcription, post transcription, or translation as described in Kooter et al. (1999) *Trends Plant Science*, 4, 340-347; Denli and Hannon (2003) *Trends Biochem. Sci.* 28, 196-201; Brodersen and Voinnet (2006) *Trends Genet.* 22, 268-280; Allen et al. (2005) *Cell*, 121, 207-221; Patent Application Publication US 2006/0174380 A1; and Patent Application Publication US 2008/0066206 A1. Small RNA (sRNA) silencing pathways can be classified by the biosynthesis, biogenesis, and recognition of types of regulatory sRNAs, e.g., short interfering (si)RNAs, micro (mi)RNAs, and phased sRNAs, and by the participating sRNA silencing pathway proteins. This invention provides methods and recombinant DNA constructs for disrupting sRNA silencing when the expression of a transgene that is susceptible to sRNA silencing initiates sRNA silencing. By concomitantly transcribing RNA from DNA of a transgene and RNA from DNA from an sRNA silencing pathway gene, initiation of sRNA silencing also suppresses expression of the sRNA silencing gene. This concomitant transcription of transgene and sRNA silencing pathway gene(s) provides a means of autoregulation of expression of the transgene with less susceptibility to sRNA silencing.

Figure 1A:
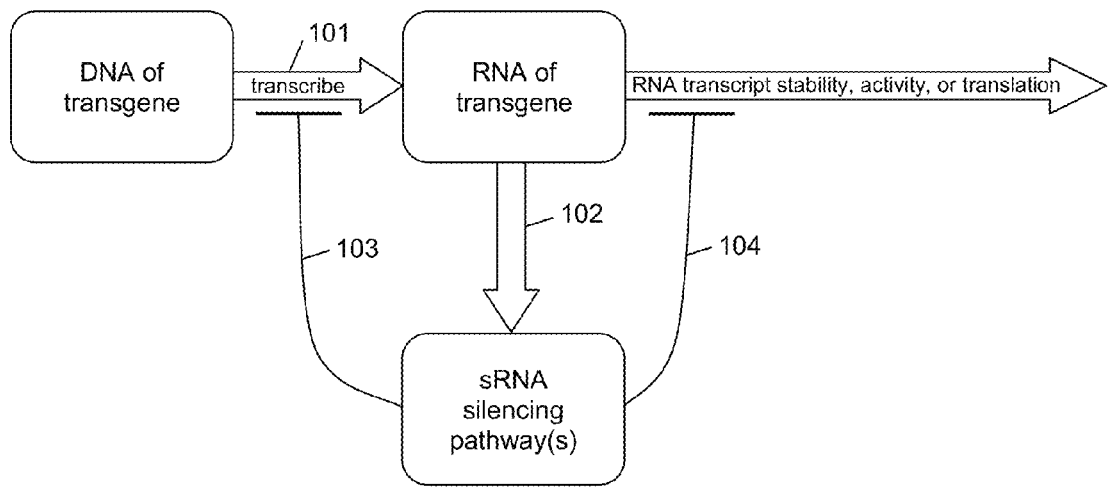
FIGS. 1A and 1B are schematic descriptions illustrating a transgene susceptible to silencing (FIG. 1A) and an aspect of the invention (FIG. 1B).
Figure 1B:
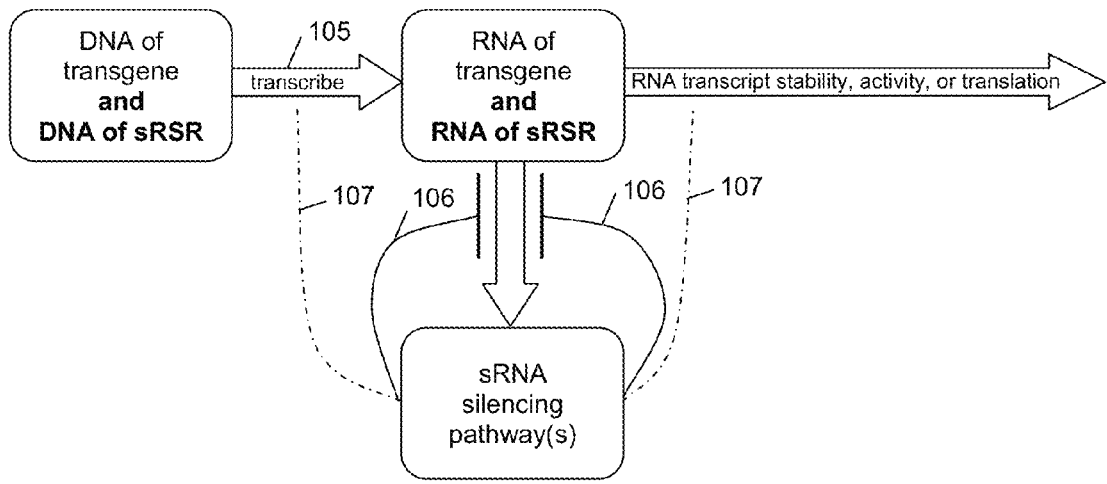

With reference to FIGS. 1A and 1B, an aspect of the invention is a method to autoregulate expression of a transgene susceptible to sRNA silencing by concomitantly transcribing RNA from DNA of a transgene and RNA from DNA from at least one sRNA silencing pathway gene. Following the transcription 101 of DNA to RNA, sRNA silencing pathways proteins can initiate 102 transgene silencing at transcription 103, post-transcription 104, or both. By concomitantly transcribing 105 RNA from DNA of the transgene and RNA from DNA of an sRNA silencing regulator (sRSR), initiation of sRNA silencing also suppresses the expression of gene(s) required for sRNA silencing 106 thereby making transgene expression less susceptible (dotted 107) to sRNA silencing.

The method of this invention that provides for transgene expression with less susceptibility to sRNA silencing can occur in a transgenic cell or a transgenic organism, e.g., a transgenic plant cell or a transgenic plant. Alternatively, when sRNA silencing of transgene-produced RNA occurs in a pest or pathogen of the transgenic plant, or in a symbiont associated with such a pest or pathogen of the transgenic plant, the method of this invention can be effected in such a pest, pathogen, or symbiont, e.g., a nematode that is controlled by RNA of the transgene produced in the roots of the transgenic plant. Thus, the targeted sRNA pathway gene(s) can be in the transgenic plant, in a pest or pathogen of the transgenic plant, or in a symbiont associated with a pest or pathogen of a transgenic plant.

Several sRNA silencing pathway genes have been identified in plants and their role in the sRNA silencing pathway elucidated to varying degrees. These sRNA silencing pathway genes are involved in transgene silencing, a limiting factor in achieving efficient transgene expression in a cell of a transgenic host, for example for highly expressed transgenes that provide herbicide and pest tolerance in transgenic plants. An sRNA silencing pathway gene includes DNA that encodes proteins that are active in or essential to the operation of an sRNA silencing pathway; such DNA can be endogenous to the organism in which sRNA silencing occurs or can be DNA from a paralog, homolog, or ortholog. Examples of known sRNA silencing pathway proteins from *Arabidopsis* are described in table 1 of Brodersen and Voinnet (2006) *Trends Genet.* 22, 268-280. Small RNA silencing pathway genes useful in this invention include genes encoding a protein with the domains/motifs and biochemical activities described in table 1 of Brodersen and Voinnet (2006). Representative sRNA silencing pathway proteins known in the art include RDR6, SDE3, RDR2, WEX, SGS3, DCL2-4, UPF1, UPF3, HEN1, NRPD1A, NRPD2, DRD1, HDA6, AGO1, and MOP1, described in Brodersen and Voinnet (2006); Arciga-Reyes et al. (2006) *The Plant Journal* 47, 480-489; Chan et al. (2005) *Nature Rev. Genet.* 6, 351-360; Matzke and Birchler (2005) *Nature Rev. Genet.* 6, 24-35; and Alleman et al. (2006) *Nature* 442, 295-298. Novel sRNA silencing pathway genes from RNA-directed RNA polymerases known in the art are also described in US Patent Application Publication 2006/0123510 A1 and US Patent Application Publication 2001/0023067 A1. A person of ordinary skill in the art can readily identify or isolate a DNA molecule that encodes for all or part of a homologous or orthologous sRNA silencing pathway protein by searching databases, cloning directly from genomic or cDNA libraries from various organisms, e.g., plants, invertebrates including insects and nematodes, fungi, and viruses, or isolating polypeptides with sRNA silencing activity, e.g., isolating a polypeptide having the enzymatic activity of an RNA-dependent RNA polymerase (RDRP).

Two sRNA silencing pathway proteins from *Zea mays* (Zm) are ZmRDR6A (SEQ ID NO: 1) and ZmRDR6B (SEQ ID NO: 2).

RDR6 is an RDRP and a component of the posttranscriptional gene silencing (PTGS) pathway in plants (See Elmayan et al. (1998) *The Plant Cell* 10, 1747-1757). Permanent shutdown of an RDR6 protein in a plant may result in undesirable effects in the plant because RDR6 is also an important protein of plant defense mechanisms, juvenile-to-adult transition, and other developmental processes as described in Schwach et al. (2005) *Plant Physiology* 138, 1842-1852; and Fahlgren et al. (2006) *Current Biology* 16, 939-944. The use of DNA from an RDR6 gene in the recombinant DNA constructs used in the practice of this invention can result in ameliorating the extent of such undesirable effects in a transgenic plant by suppressing RDR6 expression only when transgene silencing is initiated.

MOP1 is a component of the transcriptional gene silencing (TGS) pathway in maize plants where inactivation by mutation reactivates transgene expression from silenced repeat loci in maize and is required for the production of siRNAs involved in the chromatin RNAi pathway (see Alleman et al. 2006 *Nature* 442, 295-298). Alleman et al. (2006) also shows that maize plants with a mop1 mutation exhibit pleiotropic development phenotypes. The use of DNA encoding MOP1 in the recombinant DNA constructs used in the practice of this invention can result in ameliorating the extent of such undesirable phenotypes in a transgenic plant by suppressing MOP1 expression only when transgene silencing is initiated.

Methods for introducing DNA of a gene for expression in an organism and thereby calling the introduced DNA a transgene are well known and widely practiced. Additionally, various types of DNA of genes that have been used as transgenes are widely known. For instance, various types of DNA of genes used as transgenes include DNA from an endogenous gene of a eukaryote organism, from an endogenous gene of a transgenic plant, from an endogenous gene of a pest or pathogen of a plant, from an endogenous gene of a symbiont associated with a pest or pathogen of a plant, from a microRNA gene, and from a non-coding RNA gene. Aspects of this invention are useful in transgenic plants having transgene DNA that transcribes to non-coding RNA or to mRNA encoding a protein. Aspects of this invention provides transgenic plants having DNA of one or more highly expressed transgenes susceptible to silencing wherein the transgene(s) impart herbicide tolerance and/or pest tolerance.

DNA of genes that encode for proteins that impart herbicide tolerance is found in U.S. Pat. No. 4,769,061 (mutant 5-enolpyruvylshikimate-3-phosphate synthase for glyphosate herbicide tolerance), U.S. Pat. No. 5,627,061 (mutant 5-enolpyruvylshikimate-3-phosphate synthase for glyphosate herbicide tolerance), U.S. Pat. No. 5,463,175 (glyphosate oxido-reductase for glyphosate herbicide tolerance), U.S. Pat. No. 5,646,024 (phosphinothricin acetyltransferase for glufosinate herbicide tolerance), U.S. Pat. No. 5,767,366 (a mutant acetolactate synthase for imidazolinone herbicide tolerance), U.S. Pat. No. 4,810,648 (haloarylnitrilase for bromoxynil herbicide tolerance), U.S. Pat. No. 6,414,222 (acetyl-coenzyme A carboxylase for cyclohexanedione or aryloxyphenoxypropanoic acid herbicide tolerance), U.S. Pat. No. 5,597,717 (modified dihydropteroate synthase for sulfonamide herbicide resistance), US Patent Application Publication 2003/0083480A1 (glyphosate-N-acetyl transferase for glyphosate herbicide tolerance), US Patent Application Publication 2003/0115626A1 (dicamba mono-oxygenase for dicamba herbicide tolerance), and US Patent Application Publication 2004/0200874A1 (glyphosate decarboxylase for glyphosate herbicide tolerance), incorporated herein by reference. See also International Application WO 99/27116 (2,2-dichloropropionic acid dehalogenase for dalapon herbicide resistance).

Bacterial DNA encoding proteins that impart pest tolerance, e.g., the *Bacillus thuringiensis* Cry1A(b), Cry1A(c), Cry3Aa, Cry1Ca, and Cry2Aa delta-endotoxins, for use in transgenes are found in U.S. Pat. Nos. 5,500,365 and 5,689,052, incorporated herein by reference. Insect tolerance genes include any of a number of natural or codon-optimized DNA from *Bacillus thuringiensis* for encoding an insect toxin protein, e.g., a Lepidopteran or Coleopteran insect toxin protein, i.e., *Bacillus thuringiensis* Cry1A(b) endotoxin, *Bacillus thuringiensis* Cry2Aa endotoxin, *Bacillus thuringiensis* Cry3A endotoxin, or ET29 and TIC810 endotoxins. US Patent Application Publication 2007/022897, incorporated herein by reference, discloses DNA encoding endotoxins that are toxic to lepidopteran and coleopteran insects. Pest tolerance genes include DNA from an insect that transcribes to insect-toxic RNA, i.e., RNA that becomes a double-stranded RNA (dsRNA) targeting a vacuolar ATPase gene of soybean cyst nematode, or nematode-toxic RNA that becomes a dsRNA targeting a soybean cyst nematode major sperm protein, as disclosed in US Patent Application Publication 2008/0201801 A1, incorporated herein by reference.

An sRNA silencing regulator (sRSR) is DNA that includes identical or similar DNA, e.g., about 80%, 81%, 82%, 83%, 84%, 85%, 86%, 87%, 88%, 89%, 90%, 91%, 92%, 93%, 94%, 95%, 96%, 97%, 98%, 99%, 100%, from a fragment of or all of the gene that encodes at least one sRNA silencing pathway protein, or the DNA complement thereof. A fragment of an sRNA silencing pathway gene can comprise at least 18 or more nucleotides, e.g., at least 18 or 19 or 20 or 21 or 22 or 23 or 24 or 25 or up to 50 or more nucleotides, from about 50 to about 1000 or more nucleotides up to the complete cDNA size, from about 50 to about 100, from about 50 to about 200, from about 100 to about 228, from about 100 to about 500, or from about 166 to about 272 nucleotides. The sRNA silencing regulator (sRSR) is transcribed to RNA that is sufficiently similar or complementary to an sRNA silencing pathway gene to allow the sRSR transcript to bind in a cell to a fragment or all of the RNA transcribed for the sRNA silencing pathway protein. In some aspects of the invention, concomitant transcription of DNA of the transgene and DNA of the sRSR may be achieved under the regulation of one or more promoters, e.g., a single promoter selected to concomitantly regulate transcription of the transgene and the sRSR.

Those skilled in the art will recognize that some nucleotide sequences useful for the sRNA silencing regulator (sRSR) will have higher intrinsic silencing ability than others. There are a variety of computational tools available to help predict silencing efficacy and to help modify the sRNA silencing regulator nucleotide sequence to eliminate potential protein translation and potential splice donors/acceptors and polyadenylation signals. See, e.g., Reynolds et al. 2004 *Nature Biotechnology* 22, 326-330 and Khvorova et al. 2003 *Cell* 115, 209-216. Alternatively, empirical methods for determining the silencing efficacy of nucleotide sequences from sRNA silencing pathway genes in the method of this invention were disclosed in US Patent Application Publication 2007/0192903 A1 and in US Patent Application Publication 2009/0117539 A1, incorporated herein by reference.

In an aspect of the invention the sRNA silencing regulator (sRSR) comprises a contiguous DNA sequence formed by concatenation of DNA segments from more than one sRNA silencing pathway gene and/or multiple fragments from a single sRNA silencing pathway gene. The concatenated parts of such an sRSR can be concatenated in sense, antisense, or a combination of both orientations. The DNA of the concatenated sRSR can be transcribed in sense or antisense orientations.

In various embodiments of the recombinant DNA construct that includes DNA of a transgene and DNA of an sRNA silencing regulator (sRSR), the sRSR is located in a region that is 5' to the transgene, 3' to the transgene, in the transgene, 5' to the transcription termination site, 3' to the transcription initiation site, or embedded in an intron. In some embodiments, the recombinant DNA construct includes more than one sRSR located in more than one position of the recombinant DNA construct. FIG. 2E illustrates multiple possible embodiments of the invention relative to the position of the sRSR and the positions of the promoter, the 3' untranslated region (UTR), and the transgene.

Figure 2A:
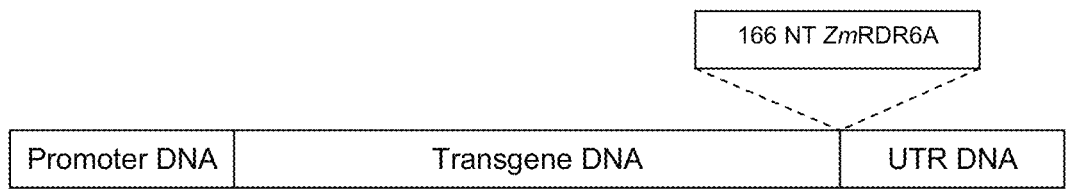
FIGS. 2A through 2E illustrate recombinant DNA constructs.
Figure 2B:
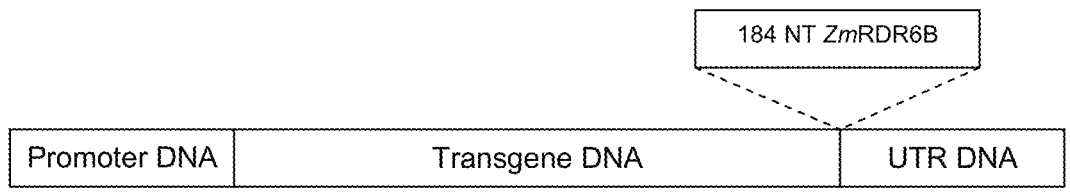

With reference to FIG. 3, an aspect of the invention is illustrated using the recombinant DNA construct of FIGS. 2A and 2B. The first step in each subview of FIG. 3 (310 and 320) involves the transcription of the recombinant DNA construct to RNA.

Figure 3A:
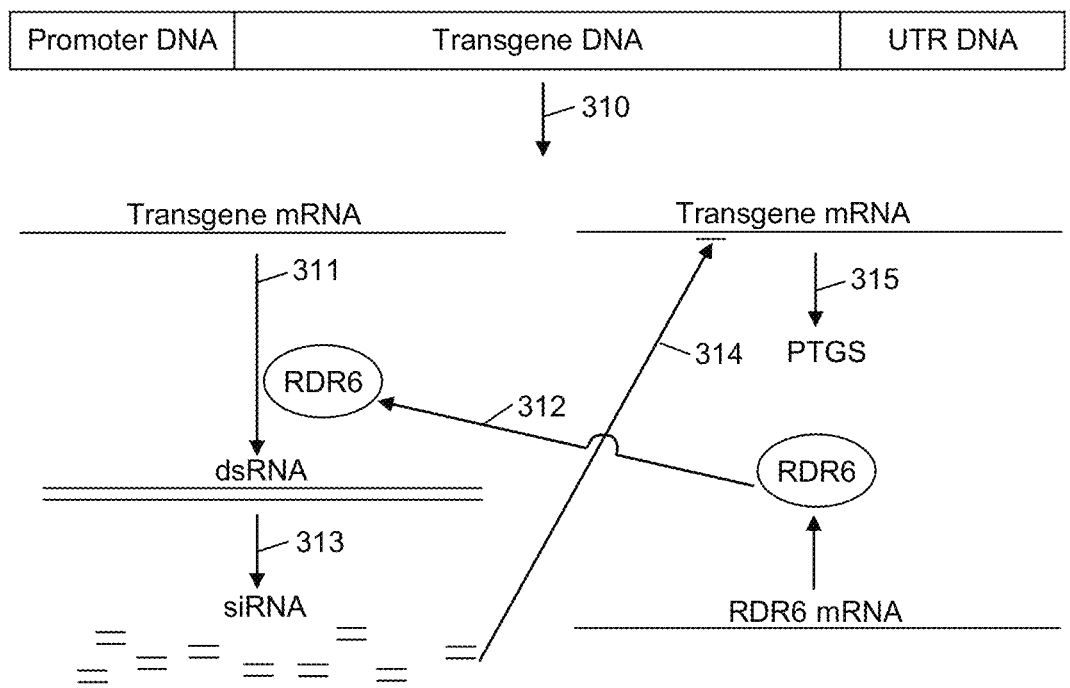
FIGS. 3A and 3B are pathway diagrams illustrating a transgene susceptible to silencing (FIG. 3B) and an aspect of the invention (FIG. 3B).

FIG. 3A illustrates an aspect of an sRNA silencing pathway when a transgene is susceptible to PTGS. Following transcription to messenger RNA (mRNA), PTGS initiating transgene mRNA initiates a PTGS pathway 311 through an RDR6-dependents RNA silencing pathway 312 which biosynthesizes double-stranded (ds)RNA from mRNA. Following biosynthesis is biogenesis 313 of small-interfering (si)RNA from dsRNA to by other sRNA silencing pathway proteins. Following biogenesis is siRNA recognition and cleavage of mRNA by other sRNA silencing pathway proteins 314, ultimately leading to PTGS 315 of the transgene.

Figure 3B:
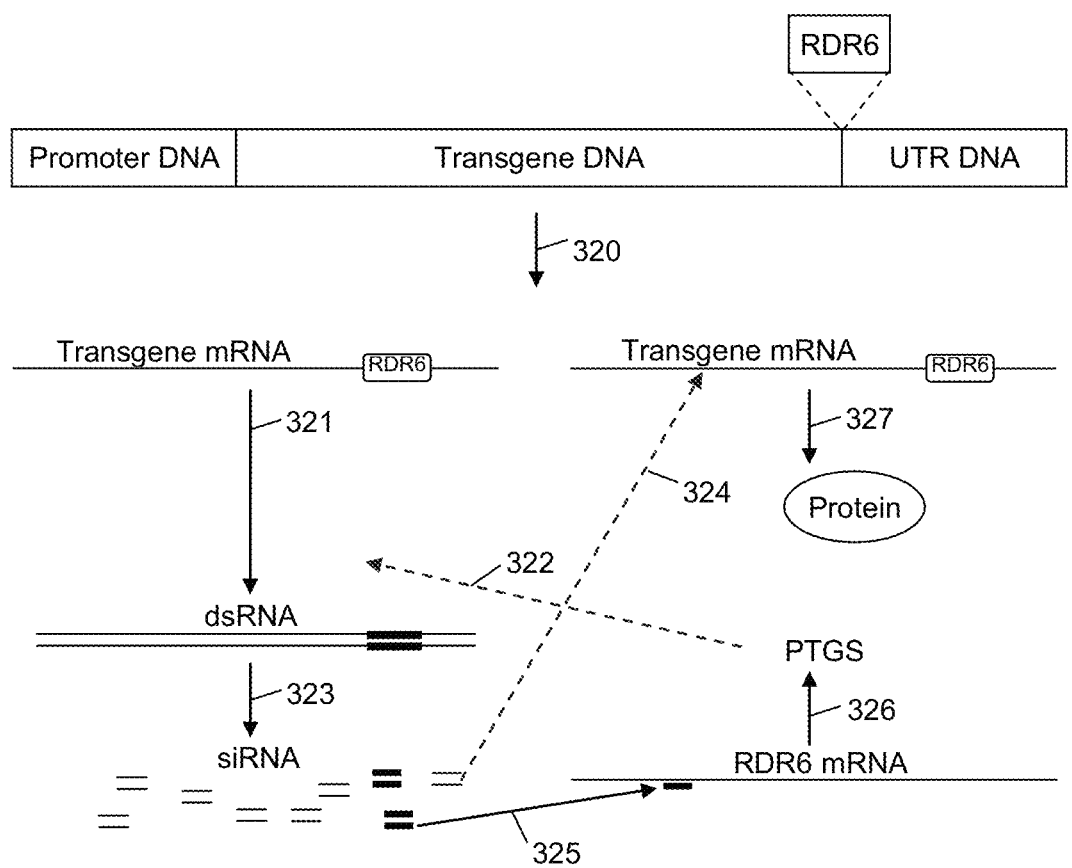

FIG. 3B illustrates an aspect of this invention when DNA of a transgene and DNA of RDR6 are concomitantly transcribed 320. Biosynthesis 321 of transgene mRNA and RDR6RNA produces dsRNA of transgene and RDR6 (shown as double-stranded thin and thick lines, respectively). Biogenesis 323 of siRNA from dsRNA produces siRNA that recognizes 325 and inhibits 326 RDR6 by PTGS. As RDR6 expression is suppressed, transgene expression becomes less susceptible to sRNA silencing pathways 322/324 (dotted lines) thereby allowing for transgene expression 327 to protein.

Another aspect of the invention provides for a recombinant cell having in its genome the recombinant DNA construct that includes a transgene and an sRNA silencing regulator. The recombinant cell may be isolated, e.g., at transformation, part of a cell culture of transformed cells, or part of a differentiated organism, e.g., a transgenic plant, or in cells of plant tissue that survive due to autoregulation of a transgene that is susceptible to silencing. The invention further provides a transgenic organism including a transgenic plant cell, plant, pollen or seed having a recombinant DNA construct with DNA for autoregulating transgene expression and commodity products prepared from such a transgenic organism, for example, transgenic plant biomass, transgenic plant meal, transgenic plant seed, transgenic plant leaves, transgenic plant flour, and transgenic plant stalk.

An aspect of the invention is the transient expression of the recombinant DNA construct that includes a transgene and an sRNA silencing regulator in a plant. Such transient expression is typically not heritable to a progeny plant. Another aspect of the invention is the stable integration of the recombinant DNA construct that includes a transgene and an sRNA silencing regulator into the genome of a transgenic plant cell, plant, pollen or seed. Stable integration into the genome of a plant means that the recombinant DNA is heritable in progeny plants and seeds; therefore, a further aspect of this invention includes regenerated transgenic plants and transgenic progeny plants having stably integrated into their genome the recombinant DNA construct that includes a transgene and an sRNA silencing regulator. Methods for stably integrating a recombinant DNA construct of this invention into a transgenic plant are well known and widely practiced. Specific methods, including transformation methods, for inserting such recombinant DNA constructs into transgenic plant cells and regenerating transgenic plants and seeds are disclosed in example 5 of US Patent Application Publication (2011029655) of U.S. Ser. No. (12/999,777) of national phase entry (section 371) from international application PCT/US09/49392 (Publication WO 2010/002984), incorporated herein by reference.

Any suitable eukaryote may be made transgenic with a recombinant DNA construct of this invention, including domestic or wild mammals, birds, and fish; invertebrates such as arthropods and nematodes; yeasts and fungi; plants such as dicot, monocot, and plants of commercial or agricultural interest, such as crop plants, wood- or pulp-producing trees, vegetable plants, fruit plants, and ornamental plants; and pests, pathogens, or symbionts of plants. Dicot plants include, but are not limited to, canola, cotton, potato, quinoa, amaranth, buckwheat, safflower, soybean, sugarbeet, and sunflower. Monocot plants include wheat, oat, barley, maize, rye, triticale, rice, ornamental and forage grasses, sorghum, millet, and sugarcane.

In other embodiments of the invention the DNA construct that includes a transgene and an sRNA silencing regulator is located in a vector for transforming a plant cell (such as within a plasmid or viral vector), or on a biolistic particle for transforming a plant cell, or within a nuclear chromosome or plastid or mitochondrion of a non-natural transgenic plant cell, or within a non-natural transgenic cell, non-natural transgenic plant tissue, non-natural transgenic plant seed, non-natural transgenic pollen grain, a non-natural transgenic or partially transgenic plant, or a dead plant part.

The following examples serve to illustrate various aspects of the invention.

EXAMPLE 1

This example illustrates concomitant transcription of RNA from DNA of a transgene and RNA from DNA from an sRNA silencing pathway gene to autoregulate the expression of the transgene. More specifically, this example illustrates use of a recombinant DNA construct including a transgene encoding green fluorescence protein (GFP) that provides a marker for protein expression and DNA from an *N. benthamiana* RDR6 gene as an sRNA silencing regulator to autoregulate the expression of DNA encoding GFP that was transiently expressed in *N. benthamiana* (Nb) plants through agro-infiltration.

A control recombinant DNA construct was prepared including DNA of the GFP gene. The control construct was transiently expressed in Nb cells where GFP activity was observed to be susceptible to silencing from two to three days and up to six days after infiltrating the control DNA construct in an Nb leaf tissue.

Two recombinant DNA constructs of this invention were prepared with DNA encoding GFP and a nucleotide fragment of DNA cloned from NbRDR6 as the sRNA silencing regulator (sRSR). In one construct the cloned nucleotide fragment from NbRDR6 was sense in orientation (SEQ ID NO: 3), and in the other construct the cloned nucleotide fragment was antisense in orientation (SEQ ID NO: 4). Each construct was transiently expressed in Nb cells for six days where GFP activity was measured and observed to be less susceptible to silencing compared to Nb cells with the control DNA construct.

EXAMPLE 2

This example illustrates concomitant transcription of RNA from DNA of a transgene and RNA from DNA from an sRNA silencing pathway gene to autoregulate the expression of the transgene where the transgene encodes a 5-enolpyruvylshikimate-3-phosphate synthase (EPSPS) that imparts glyphosate herbicide tolerance to transgenic plants and DNA from a *Zea mays* RDR6 gene is used as an sRNA silencing regulator (sRSR) to autoregulate the expression of DNA encoding EPSPS that is stably transformed in *Zea mays* plants.

Figure 4A:
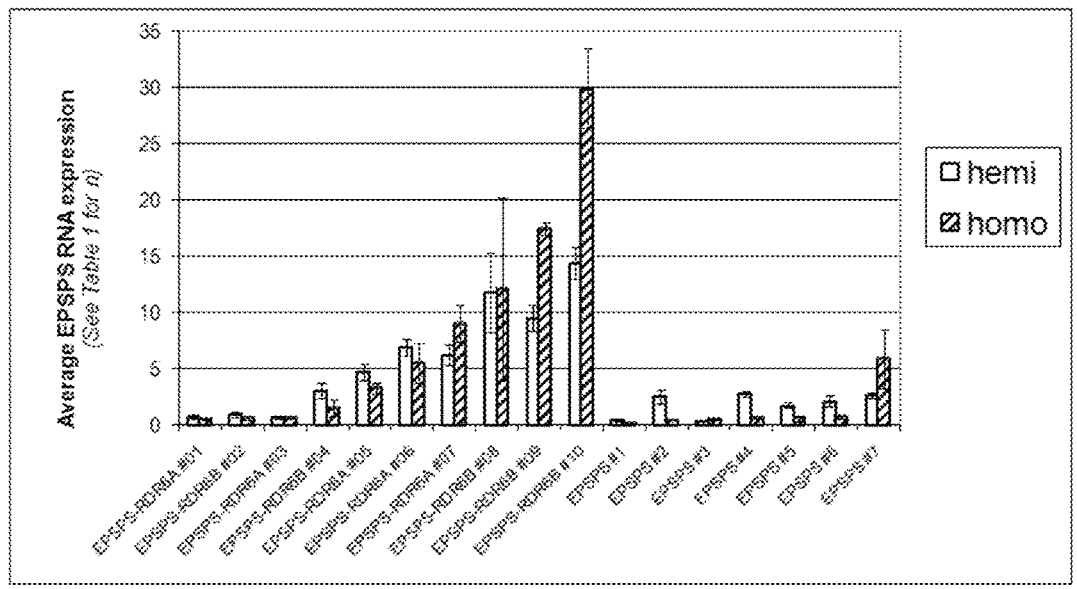
FIGS. 4A and 4B are bar charts showing RNA expression data related to use of the invention illustrated in examples 2 and 3.

A control recombinant DNA construct was prepared including promoter DNA from the sugarcane badnavirus bacilliform plant virus linked to DNA encoding EPSPS (identified as "EPSPS" in Table 1 and FIG. 4A). The control construct was stably integrated into maize cells to provide 7 distinct transgenic events of transgenic maize cells with random insertion of a single copy of the control recombinant DNA construct in the maize genome. The transgenic maize cells were regenerated and propagated into transgenic plants for each control event (identified as EPSPS #1 through EPSPS #7 in Table 1 and FIG. 4A). Progeny transgenic seed from each control event were used to produce progeny control transgenic plants that were hemizygous or homozygous for the control EPSPS construct. Transcribed RNA of EPSPS was measured in hemizygous and homozygous control plants.

With reference to FIGS. 2A and 2B two recombinant DNA constructs were prepared including a sugar cane badnavirus bacilliform plant virus promoter linked to DNA encoding EPSPS and a nucleotide fragment of DNA from ZmRDR6 as an sRNA silencing regulator (sRSR). In one construct a 166 nucleotide fragment (SEQ ID NO: 5) was taken from ZmRDR6A, and in the other construct a 184 nucleotide fragment (SEQ ID NO: 6) was taken from ZmRDR6B (constructs identified in Table 1 and FIG. 4A as "EPSPS-ZmRDR6A" and "EPSPS-ZmRDR6B"). Each recombinant DNA construct was stably transformed into multiple maize cells to provide 10 distinct events of transgenic cells with a random insertion of a single copy of the recombinant DNA construct in the maize genome. Transgenic maize cells were regenerated and propagated into transgenic plants for each distinct EPSPS-RDR6A or EPSPS-RDR6B event (identified as #01 through #10 in Table 1 and FIG. 4A). Progeny transgenic seed from each distinct event were used to produce progeny transgenic plants that were hemizygous or homozygous for the EPSPS-ZmMOP1 constructs. The DNA producing transcribed RNA of EPSPS in plants with the EPSPS-ZmRDR6 constructs were observed in hemizygous and homozygous plants to be less susceptible to silencing compared to control plants with the EPSPS control construct. Table 1 reports the average expression of EPSPS RNA in the hemizygous and homozygous plants for each transgenic event where "n" represents the number of plants evaluated per event.

TABLE 1

| DNA construct | Hemizygous (hemi) | | Homozygous (homo) | |
|---|---|---|---|---|
| | Expression | n | Expression | n |
| EPSPS-RDR6A #01 | 0.78 | 11 | 0.54 | 8 |
| EPSPS-RDR6B #02 | 1.00 | 7 | 0.60 | 9 |
| EPSPS-RDR6A #03 | 0.69 | 13 | 0.63 | 5 |
| EPSPS-RDR6B #04 | 3.09 | 15 | 1.53 | 3 |
| EPSPS-RDR6A #05 | 4.71 | 14 | 3.30 | 5 |
| EPSPS-RDR6A #06 | 6.94 | 9 | 5.56 | 8 |
| EPSPS-RDR6A #07 | 6.20 | 9 | 9.05 | 7 |
| EPSPS-RDR6B #08 | 11.81 | 10 | 12.10 | 4 |
| EPSPS-RDR6B #09 | 9.54 | 13 | 17.41 | 2 |
| EPSPS-RDR6B #10 | 14.42 | 11 | 29.94 | 11 |
| EPSPS #1 | 0.43 | 12 | 0.09 | 3 |
| EPSPS #2 | 2.54 | 10 | 0.45 | 9 |
| EPSPS #3 | 0.40 | 10 | 0.50 | 10 |
| EPSPS #4 | 2.81 | 13 | 0.58 | 11 |
| EPSPS #5 | 1.76 | 12 | 0.62 | 4 |
| EPSPS #6 | 2.13 | 6 | 0.71 | 5 |
| EPSPS #7 | 2.63 | 13 | 5.87 | 8 |

With reference to FIG. 4A, average levels of EPSPS RNA expression in hemizygous (hemi) and homozygous (homo) progeny plants for an event are represented by a pair of bars with error brackets representing the standard error (standard deviation of mean divided by the square root of n). The data in Table 1 and FIG. 4A show that the average EPSPS RNA expression in four out of ten EPSPS-RDR6A or EPSPS-RDR6B events in homozygous plants (#07 through #10) were higher than that of the highest average homozygous control (EPSPS #7). The data in Table 1 and FIG. 4A also show that the average EPSPS RNA expression in seven out of ten EPSPS-RDR6A or EPSPS-RDR6B events in homozygous plant (#04 through #10) were higher than that of the second highest average homozygous control (EPSPS #6). The average EPSPS RNA expression of the highest EPSPS-RDR6 homozygous plant (EPSPS-RDR6B #10) was 5-fold greater than in the highest average homozygous control (EPSPS #7).

EXAMPLE 3

This example illustrates concomitant transcription of RNA from DNA of a transgene and RNA from DNA from an sRNA silencing pathway gene to autoregulate the expression of the transgene where the transgene encodes a 5-enolpyruvylshikimate-3-phosphate synthase (EPSPS) that imparts glyphosate herbicide tolerance to transgenic plants and DNA from a *Zea mays* MOP1 gene is used as an sRNA silencing regulator (sRSR) to autoregulate the expression of DNA encoding EPSPS that is stably transformed in *Zea mays* plants.

Figure 4B:
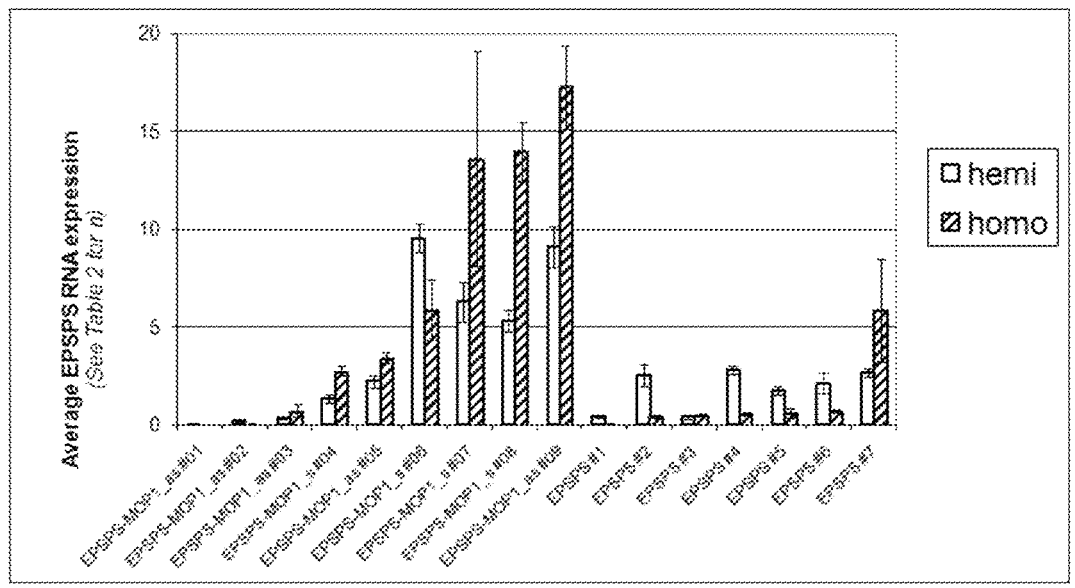

A control recombinant DNA construct was prepared including promoter DNA from the sugarcane badnavirus bacilliform plant virus linked to DNA encoding EPSPS (identified as "EPSPS" in Table 2 and FIG. 4B). The control construct was stably integrated into maize cells to provide 7 distinct transgenic events of transgenic maize cells with random insertion of a single copy of the control recombinant DNA construct in the maize genome. The transgenic maize cells were regenerated and propagated into transgenic plants for each control event (identified as EPSPS #1 through IPSPS #7 in Table 2 and FIG. 4B). Progeny transgenic seed from each control event were used to produce progeny control transgenic plants that were hemizygous or homozygous for the control EPSPS construct. Transcribed RNA of EPSPS was measured in hemizygous and homozygous control plants.

Figure 2C:
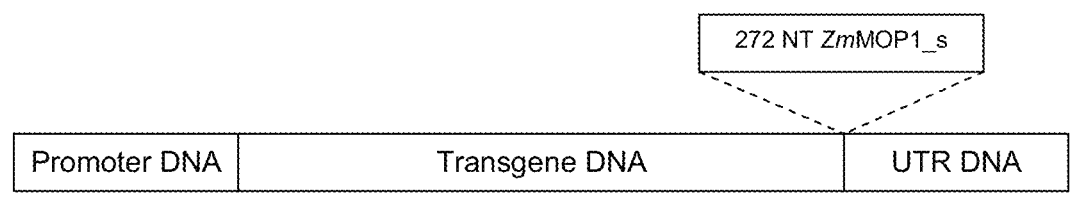
Figure 2D:
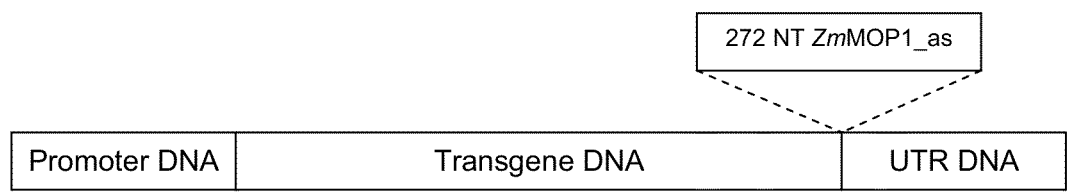
Figure 2E:
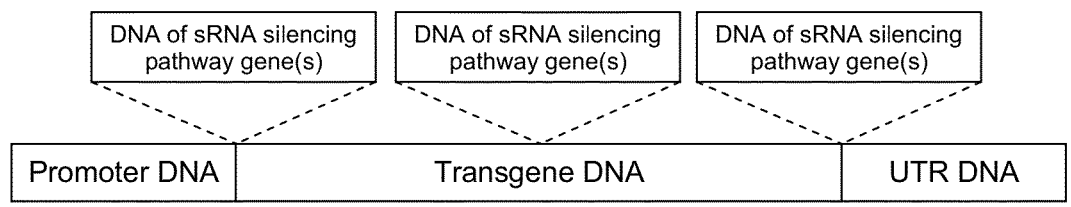

With reference to FIGS. 2C and 2D two recombinant DNA constructs were prepared including a sugarcane badnavirus bacilliform plant virus promoter linked to DNA encoding EPSPS and a 272 nucleotide fragment of DNA from ZmMOP1 (SEQ ID NO: 7) as an sRNA silencing regulator (sRSR). In one construct the 272 nucleotide fragment from ZmMOP1 was prepared in the sense (_s) orientation, and in the other construct it was prepared in the antisense (_as) orientation (constructs identified in Table 2 and FIG. 4B as "EPSPS-ZmMOP1_s" and "EPSPS-ZmMOP1_as"). Each recombinant DNA construct was stably transformed into multiple maize cells to provide 9 distinct events of transgenic cells with a random insertion of a single copy of the recombinant DNA construct in the maize genome. Transgenic maize cells were regenerated and propagated into transgenic plants for each distinct EPSPS-MOP1_a or EPSPS-MOP1_as event (identified as #01 through #09 in Table 2 and FIG. 4B). Progeny transgenic seed from each distinct event were used to produce progeny transgenic plants that were hemizygous or homozygous for the EPSPS-ZmMOP1 constructs. The DNA producing transcribed RNA of EPSPS in plants with the EPSPS-ZmMOP1 constructs were observed in hemizygous and homozygous plants to be less susceptible to silencing compared to plants with the EPSPS control construct. Table 2 reports the average expression of EPSPS RNA in the hemizygous and homozygous plants for each transgenic event where "n" represents the number of plants evaluated per event.

TABLE 2

| DNA construct | Hemizygous (hemi) Expression | n | Homozygous (homo) Expression | n |
|---|---|---|---|---|
| EPSPS-MOP1_as #01 | 0.01 | 7 | 0.02 | 8 |
| EPSPS-MOP1_as #02 | 0.22 | 14 | 0.08 | 3 |
| EPSPS-MOP1_as #03 | 0.34 | 13 | 0.72 | 3 |
| EPSPS-MOP1_s #04 | 1.32 | 11 | 2.74 | 8 |
| EPSPS-MOP1_as #05 | 2.21 | 9 | 3.42 | 8 |
| EPSPS-MOP1_s #06 | 9.54 | 8 | 5.89 | 8 |
| EPSPS-MOP1_s #07 | 6.27 | 16 | 13.60 | 2 |
| EPSPS-MOP1_s #08 | 5.34 | 9 | 13.96 | 6 |
| EPSPS-MOP1_as #09 | 9.11 | 12 | 17.24 | 4 |
| EPSPS #1 | 0.43 | 12 | 0.09 | 3 |
| EPSPS #2 | 2.54 | 10 | 0.45 | 9 |
| EPSPS #3 | 0.40 | 10 | 0.50 | 10 |
| EPSPS #4 | 2.81 | 13 | 0.58 | 11 |
| EPSPS #5 | 1.76 | 12 | 0.62 | 4 |
| EPSPS #6 | 2.13 | 6 | 0.71 | 5 |
| EPSPS #7 | 2.63 | 13 | 5.87 | 8 |

With reference to FIG. 4B, average levels of EPSPS RNA in hemizygous (hemi) and homozygous (homo) progeny plants from an event are represented by a pair of bars with error brackets representing the standard error (standard deviation of mean divided by the square root of n). The data in Table 2 and FIG. 4B show that the average EPSPS RNA expression in four out of nine EPSPS-MOP1_a or EPSPS-MOP1_as events in homozygous plants (#06 through #09) were higher than that of the highest average homozygous control (EPSPS #7). The data in Table 2 and FIG. 4B also show that the average EPSPS RNA expression in seven out of ten EPSPS-MOP1_a or EPSPS-MOP1_as events in homozygous plants (#03 through #09) were higher than that of the second highest average homozygous control (EPSPS #6). The average EPSPS RNA expression of the highest EPSPS-MOP1 homozygous plant (EPSPS-MOP1_as #09) was 3-fold greater than the highest average homozygous control (EPSPS #7).

EXAMPLE 4

To further illustrate aspects of the invention where concomitant transcription of RNA from DNA of a transgene and RNA from DNA from an sRNA silencing pathway gene autoregulates the expression of the transgene, this example shows the use of different recombinant DNA constructs including DNA of a transgene and DNA from a gene encoding one of the sRNA silencing pathway proteins selected from an RDR6, SDE3, RDR2, WEX, SGS3, DCL2-4, UPF1, UPF3, HEN1, NRPD1A, NRPD2, DRD1, HDA6, MOP1, and AGO1.

A control recombinant DNA construct is made to include DNA from a CaMV 35S promoter linked to DNA encoding EPSPS. Separate recombinant DNA constructs are made each combining DNA from a CaMV 35S promoter linked to DNA encoding EPSPS and DNA from an sRNA silencing pathway gene for each of the RDR6, SDE3, RDR2, WEX, SGS3, DCL2-4, UPF1, UPF3, HEN1, NRPD1A, NRPD2, DRD1, HDA6, MOP1, and AGO1 sRNA silencing pathway proteins. Each construct by itself is stably integrated into maize plant cells that are regenerated into transgenic maize plants and progeny seed and progeny plants in a manner similar to that described in example 2 resulting in distinct plants and seed for each recombinant DNA construct. Transgene expression of EPSPS RNA is less susceptible to silencing in transgenic maize plants having cells with the recombinant DNA constructs of the invention as compared to transgenic cells with the control DNA construct.

EXAMPLE 5

To further illustrate aspects of the invention where concomitant transcription of RNA from DNA of a transgene and RNA from DNA from an sRNA silencing pathway gene autoregulates the expression of the transgene, recombinant DNA constructs are made and evaluated as in example 4 except that the recombinant DNA constructs are stably integrated into the genome of soybean, cotton, canola (rape seed), sugarcane, wheat, rice, sugar beet, potato, and alfalfa plant cells, from which transgenic plants are subsequently generated. Transgene expression of EPSPS RNA is less susceptible to silencing in transgenic plant cells with the recombinant DNA constructs of the invention compared to the EPSPS RNA expression in transgenic plant cells with the control DNA construct.

EXAMPLE 6

To further illustrate aspects of the invention, separate recombinant DNA constructs are prepared and evaluated as in example 4 except that the transgene comprises a rice actin promoter linked to DNA encoding a *Bacillus thuringiensis* (Bt) Cry1A(b) endotoxin protein that is toxic to Lepidopteran insects and the transgenic plants are maize. Transgene expression of Bt protein RNA is less susceptible to silencing in transgenic maize plant cells with a recombinant DNA construct also comprising DNA from an sRNA silencing pathway gene compared to the Bt protein RNA expression in transgenic maize plant cells without the DNA from an sRNA silencing pathway gene.

EXAMPLE 7

To further illustrate aspects of the invention, separate recombinant DNA constructs are prepared and evaluated as in examples 4 and 5 for different transgenes where DNA of the transgene encodes one of glyphosate oxido-reductase, phosphinothricin acetyltransferase, mutant acetolactate synthase, haloarylnitrilase, acetyl-coenzyme A carboxylase, modified dihydropteroate synthase, glyphosate-N-acetyl transferase, dicamba mono-oxygenase, glyphosate decarboxylase, and 2,2-dichloropropionic acid dehalogenase, which are proteins that impart herbicide tolerance to transgenic plants. Transgene expression of herbicide tolerant protein RNA is less susceptible to silencing in transgenic plants having cells with a recombinant DNA construct also comprising DNA from an sRNA silencing pathway gene compared to the RNA expression in transgenic plant cells without the DNA from an sRNA silencing pathway gene.

EXAMPLE 8

To further illustrate aspects of the invention, separate recombinant DNA constructs are prepared and evaluated as in examples 4 and 5 for different transgenes where DNA of the transgene encodes one of *Bacillus thuringiensis* Cry2Aa endotoxin and *Bacillus thuringiensis* Cry3A endotoxin, which are proteins that impart insect resistance to transgenic cotton and potato plants, respectively. Transgene expression of insecticidal protein RNA is less susceptible to silencing in transgenic cotton and potato plants having cells with a recombinant DNA construct also comprising DNA from an sRNA silencing pathway gene compared to the RNA expression in transgenic cotton and potato plant cells without the DNA from an sRNA silencing pathway gene.

EXAMPLE 9

To further illustrate an aspect of the invention, a recombinant DNA construct is prepared and evaluated as in example 4 for a transgene comprising DNA encoding cold shock protein from *Bacillus subtilis* (Bs), which is a protein that imparts drought tolerance to transgenic maize plants. Expression of Bs cold shock protein RNA is less susceptible to silencing in transgenic plants having cells with a recombinant DNA construct also comprising DNA from an sRNA silencing pathway gene compared to the RNA expression in transgenic plant cells without the DNA from an sRNA silencing pathway gene.

What is claimed is:

1. A method to autoregulate expression of a transgene susceptible to sRNA silencing by concomitantly transcribing an RNA transcript from a recombinant DNA construct inserted in the genome of a plant cell, said recombinant DNA construct comprising said transgene and at least one plant sRNA silencing pathway gene,
   wherein said at least one plant sRNA silencing pathway gene is selected from the group consisting of RDR6 and MOP1,
   wherein said transgene and at least one plant sRNA silencing pathway gene are transcribed to a single transcript, and
   wherein expression of said at least one plant sRNA silencing pathway gene is suppressed only when silencing of said transgene is initiated.

2. The method of claim 1 wherein said transgene is DNA that transcribes to an mRNA encoding a protein or to a non-coding RNA.

3. The method of claim 2 wherein said transgene comprises DNA encoding a protein that imparts herbicide tolerance or pest tolerance to a plant.

4. The method of claim 3 wherein said protein that imparts herbicide tolerance is selected from the group consisting of EPSP synthase, glyphosate oxido-reductase, phosphinothricin acetyltransferase, mutant acetolactate synthase, haloarylnitrilase, acetylcoenzyme A carboxylase, modified dihydropteroate synthase, glyphosate-N-acetyl transferase, dicamba mono-oxygenase, glyphosate decarboxylase, and 2,2-dichloropropionic acid dehalogenase.

5. The method of claim 3 wherein said protein that imparts pest tolerance is selected from the group consisting of Bacillus thuringiensis Cry1A(b) endotoxin, Bacillus thuringiensis Cry2Aa endotoxin, Bacillus thuringiensis Cry3A endotoxin, ET29 and TIC810 endotoxins, RNA that becomes a dsRNA targeting a vacuolar ATPase gene of soybean cyst nematode, and RNA that becomes a dsRNA targeting a soybean cyst nematode major sperm protein.

6. A recombinant DNA construct comprising a transgene and a heterologous sRNA silencing regulator wherein said heterologous sRNA silencing regulator comprises DNA from at least one plant sRNA silencing pathway gene selected from the group consisting of RDR6 and MOP1;
   wherein said recombinant DNA construct further comprises a plant-expressible promoter that concomitantly transcribes said transgene and said plant sRNA silencing regulator to a single transcript;
   wherein said sRNA silencing regulator is located within at least one of:
   (a) a region 5' to said transgene,
   (b) a region 3' to said transgene, and
   (c) a region within said transgene; and
   wherein said recombinant DNA construct is stably integrated in the genome of a plant cell, and
   wherein expression of said at least one plant sRNA silencing pathway gene is suppressed only when silencing of said transgene is initiated.

7. A recombinant cell having in its genome the recombinant DNA construct of claim 6.

8. A transgenic plant regenerated from said recombinant cell of claim 7, or a progeny transgenic plant of said regenerated transgenic plant, wherein said transgenic plant or progeny transgenic plant comprises the recombinant DNA construct.

9. A transgenic plant comprising a recombinant cell having in its genome the recombinant DNA construct of claim 6.

10. A commodity product prepared from the transgenic plant of claim 9, wherein said commodity product comprises said recombinant DNA construct.

11. The commodity product of claim 10 wherein said commodity product is plant biomass, plant meal, plant seed, plant leaves, plant flour, or plant stalk.

\* \* \* \* \*